United States Patent
Van Wijk et al.

(10) Patent No.: US 6,330,481 B1
(45) Date of Patent: Dec. 11, 2001

(54) TEMPORARY MEDICAL ELECTRICAL LEAD HAVING BIODEGRADABLE ELECTRODE MOUNTING PAD

(75) Inventors: Frank Van Wijk, Hoensbroek; Berthold Kramm, Cadier En Keer; Leo Kretzers, Sittard; Marc Hendriks, Brunssum, all of (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/411,846

(22) Filed: Oct. 4, 1999

(51) Int. Cl.$^7$ .................................................. A61N 1/05
(52) U.S. Cl. .............................................................. 607/129
(58) Field of Search ........................... 607/115–116, 129, 607/130, 132, 148, 149, 152; 600/372–375, 377, 393, 395; 128/DIG. 8

(56) References Cited

U.S. PATENT DOCUMENTS

| | | | |
|---|---|---|---|
| 4,963,146 | * 10/1990 | Li | 128/DIG. 8 |
| 5,203,348 | * 4/1993 | Dahl et al. | 607/129 |
| 5,849,033 | * 12/1998 | Mehmanesh et al. | 607/129 |
| 5,928,278 | * 7/1999 | Kitschmann | 607/129 |

* cited by examiner

Primary Examiner—Kennedy Schaetzle
Assistant Examiner—Kristen Droesch
(74) Attorney, Agent, or Firm—Timothy F. Woods; Thomas G. Berry

(57) ABSTRACT

A temporary cardiac electrical stimulating lead is disclosed where the lead body thereof may be removed from inside a patient through the application of a simple pulling force exerted on its proximal end. An electrode mounting pad is located at the distal end of the lead and has a stimulating electrode mounted thereon or therein. A distal end of the electrical conductor may serve as the stimulating electrode. The electrode mounting pad is preferably capable of biodegradably dissolving or otherwise dissociating over time in human body fluids. Thus, the lead body may be detached from the electrode mounting pad through the application of a simple pulling force and removed from the patient while the electrode mounting pad remains within the patient and dissolves or otherwise dissociates over time.

8 Claims, 10 Drawing Sheets

TEMPORARY MEDICAL ELECTRICAL LEAD HAVING BIODEGRADABLE ELECTRODE MOUNTING PAD

FIELD OF THE INVENTION

The present invention relates to the field of cardiac stimulation, and more specifically to the field of stimulating cardiac tissue using a medical electrical lead.

BACKGROUND OF THE INVENTION

Atrial arrhythmias and supra ventricular tachycardias, such as atrial fibrillation, atrial flutter and atrio-ventricular re-entry, are common post-operative complications among heart surgery patients. It is estimated that during the first seven to ten days after cardiac surgery post-operative supra ventricular tachycardia occurs in up to 63 percent of patients. Aranki et al. showed that patients with postoperative atrial fibrillation have a mean hospital stay of about fifteen days, whereas those patients without post-operative atrial fibrillation have a mean hospital stay of about ten days. Whether such extended hospitalization stays are primarily caused by arrhythmias is not known. See Cardiac Surg. Kirklin J W, Barrat-Boyes BC (Eds.): NY 1993, pg. 210, "The Importance of Age as a Predicator of Atrial Fibrillation and Flutter after Coronary Artery Bypass Grafting", Leitch et al., J. Thorac. Cardiovasc. Surg., 1990:100:338–42; "Atrial Activity During Cardioplegia and Postoperative Arrhythmias", Mullen et al., J. Thorac. Cardiovasc. Surg., 1987:94:558–65.

The presence of such arrhythmias, which in otherwise healthy patients may not be unduly serious, may be especially harmful to heart surgery patients. The surgery itself, the effects of prolonged anesthesia, or both have often already compromised the hemodynamic condition of such patients. Drugs that might be used to prevent post-operative atrial fibrillation are often only partially effective and may have negative effects on cardiac pump function.

Supra ventricular tachycardias may further cause a very irregular ventricular rate, which in turn can lead to hemodynamic conditions deteriorating even further. Such deterioration is especially serious for patients having a compromised left ventricular function. Such complications may also present a serious impediment to the recovery of the patient. See, for example, "Maintenance of Exercise Stroke Volume During Ventricular Versus Atrial Synchronous Pacing: Role of Contractility", Ausubel et al., Circ., 1985:72(5):1037–43; "Basic Physiological Studies on Cardiac Pacing with Special Reference to the Optimal Mode and Rate After Cardiac Surgery", Bailer et al., Thorac. Cardiovasc. Surg., 1981:29:168–73.

Due to the serious and potentially life threatening nature of the foregoing conditions, post-operative treatment is often aimed at preventing arrhythmias, such as through the use of drugs. Drugs, however, have been found not always to be effective at preventing arrhythmias. Thus, it is often necessary to provide a means for terminating any arrhythmias, which may occur. One common such means is over-pacing, more about which we say below.

If post-operative atrial fibrillation proves to have unacceptable hemodynamic consequences or causes serious symptoms, and if it does not stop spontaneously or antiarrhythmic drugs are ineffective in treating it, external cardioversion or atrial defibrillation may be required. But external atrial defibrillation, although generally effective as a treatment, may have profound side effects. First, and in contrast to ventricular defibrillation where conversion to normal sinus rhythm may occur after the first shock, atrial defibrillation may not be obtained until after several shocks have been delivered to the patient. This is because ventricular contraction continues during supra ventricular tachycardia. Due to the large amounts of energy, which must be delivered in external defibrillation (e.g., 40 to 360 Joules), the shocks are not tolerated well by conscious patients. External defibrillation is therefore preferably performed under general anesthesia or at least when the patient is sedated. The use of anesthesia gives rise to yet another patient risk factor.

External defibrillation requires relatively high energy because the electrical source is not positioned directly upon the cardiac tissue and instead must pass through the thorax, which tends to dissipate the energy. In contrast, internally applied atrial defibrillation, such as may occur during surgery through defibrillation paddles placed directly on the heart, requires considerably less energy because the defibrillation electrical energy is applied only to the tissue that needs to be defibrillated. In fact, direct atrial defibrillation may be accomplished with only one-Joule pulses in contrast to the 40 Joule and greater pulses required for external defibrillation. See, for example, Kean D., NASPE abs. 246, PACE, April 1992, pt. II, pg. 570.

Defibrillation success rates generally depend on the amount of energy delivered. The lower amount of energy delivered, the lower the defibrillation success rate and the greater the number of shocks that must be applied to obtain successful defibrillation. By way of contrast, in direct atrial defibrillation, where energy is applied directly to the heart, the energy level can be selected such that the patient may more easily tolerate both the amount of energy delivered as well as the number of shocks required.

Waldo et al. in "Use of Temporarily Place Epicardial Atrial Wire Electrodes For The Diagnosis and Treatment of Cardiac Arrhythmias Following Open-Heart Surgery," J. Thorac. Cardiovasc. Surg., 1978, vol. 76, no. 4, pp. 558–65 disclose the use of a pair of temporary heart wires placed on the atrium to diagnose and treat arrhythmias through anti-tachycardia overdrive pacing. Specifically, temporary heart wires were sutured to the atrial walls at the time of the heart surgery. Once the patient was ready to be released from hospital, the wires were removed by traction or pulling upon the external end.

Temporary post-operative atrial and ventricular pacing with temporary heart wires has been found to successfully treat many post-operative arrhythmias. As such, the procedure has become widespread—at least 100,000 such procedures are performed each year. Several problems, however, were encountered in the system disclosed by Waldo et al., referred to above. One problem encountered was the instability of heart wires mounted within the atrial wall. Because the wall undergoes constant motion, temporary heart wire leads were found to dislodge more often than was acceptable. Secondly, the relatively thin atrial walls (especially in elderly patients) were sometimes torn when the leads were removed by traction means.

An improved method of temporarily affixing heart wires onto the atrium was achieved with the introduction of the Medtronic Model 6500 Temporary Myocardial Pacing Lead System. That lead system featured a silicone atrial fixation disk to fasten the lead to the atrium, where the silicone atrial fixation disk was permanently sutured to the atrium. The lead was positioned so that it was trapped between the disk and atrial tissue. The lead could then be removed by simply pulling it from between the disk and the tissue. The rubber disk remained in the body after removal of the electrodes. The advantages offered by such a fixation system included more reliable lead fixation along with protecting the relatively thin atrial walls from tearing during lead removal. Thus, the Medtronic Model 6500 Temporary Myocardial Pacing Lead permitted post-surgical temporary anti-tachycardia over-drive pacing to be performed more safely.

Temporary anti-tachy overdrive pacing is not, however, always effective in terminating postoperative atrial arrhythmias or supra ventricular tachycardias. When drugs and overdrive pacing do not prevent or terminate such arrhythmias and tachycardias, or when inotropic drug side effects are contra-indicated, it may become necessary to perform atrial defibrillation, synchronized to the R-wave of the electrogram, to terminate potentially life-threatening arrhythmias. Because of the large energies required in defibrillation, however, many prior art temporary heart wires are not suitable for such applications.

In response to the foregoing concerns and problems in the prior art, a first generation Model No. 13004 Temporary Atrial Patch Electrode (TAPE) lead was developed by MEDTRONIC, INC. as further described in U.S. Pat. No. 5,527,358 entitled "Temporary Medical Electrical Lead" to Mehmanesh et al. The Model No. 13004 was developed as a clinical research device to investigate the feasibility of reducing post-operative atrial defibrillation in patients who underwent cardiac surgery and who were at risk of developing post-operative atrial fibrillation. TAPE electrodes were placed on the free walls of the left and right atrium. The TAPE lead comprised a defibrillation lead featuring a polytetrafluoroethylene (PTFE or TEFLON) felt pad onto which three parallel stainless steel defibrillation wire electrodes were mounted. The primary purpose of the TEFLON electrode mounting pad was to reliably fix the defibrillation lead to the atrium and to protect the atrial wall from sustaining electrical damage. In a clinical setting the Model No. 13004 TAPE lead demonstrated a Mean Defibrillation Threshold (DFT) of 1.5 Joule at 160 Volts in 23 patients. The implant time per device averaged only about 3 minutes to about 5 minutes. The Model No. 13004 TAPE lead was demonstrated to be successful in terminating post-operative atrial fibrillation.

One problem discovered in using the Model No. 13004 TAPE lead was that following removal of the defibrillation electrode and lead from the atrial wall, the TEFLON electrode mounting pad remained implanted permanently within the patient, potentially leading to an increase in the risk of infection. Additionally, it was discovered that in some patients the permanently implanted electrode mounting pad might become encapsulated by dense fibrous tissue, which in turn could lead to stiffening of the atrial wall.

SUMMARY OF THE INVENTION

The present invention has certain objects. That is, various embodiments of the present invention provide solutions to one or more problems existing in the prior art respecting implantable pacing and/or defibrillation leads, including one or more of: (a) lead conductors being difficult to explant or remove from patients; (b) mounting pads that remain permanently implanted within patients following electrode explanation; (c) electrodes being in direct contact with patient's heart tissue and burning or singeing same upon the application of defibrillation pulses, and (d) electrodes having insufficient surface area to deliver effective defibrillation pulses.

Various embodiments of the present invention have certain advantages, including one or more of: (a) permitting lower defibrillation energy levels to be employed; (b) providing increased electrode surface area for defibrillation; (c) not permitting defibrillation electrodes to directly contact heart tissue; (d) providing an electrode mounting pad which does not remain permanently implanted within the human body; (e) providing an electrode mounting pad which degrades and dissolves in a patient's body after its defibrillation function has been provided; (f) a reduced pulling force being required to extract or explant the electrode wire from a patient's body; (g) permitting a patient to undergo defibrillatory shocks without anesthesia or sedation being required; (h) permitting a temporary atrial defibrillation lead to be reliably affixed to the atrium; (i) providing a temporary atrial defibrillation lead that may be safely and reliably removed from the atrium; (j) providing a temporary atrial defibrillation lead that may be safely and reliably removed from the atrium without surgical intervention, and (k) permitting defibrillation pulses to be effectively applied to a patient's heart using a single stranded, braided or other wire.

Various embodiments of the present invention have certain features, including one or more of: (a) a sinusoidally- or semi-sinusoidally-shaped electrode; (b) a single electrode wire attached to an electrode mounting pad; (c) a plurality of electrode wires attached or mounted to an electrode mounting pad; (d) an electrode mounting pad formed from a material that is biodegradable and soluble in human body fluids over time; (e) an electrode mounting pad formed from collagen; (f) a method of making a collagen electrode mounting pad and associated electrode, including the steps of freezing and drying an electrode assembly containing collagen and an electrode; (g) a method of forming a biodegradable electrode mounting pad and its associated at least one electrode; (h) methods of using, implanting and/or removing the defibrillation electrode and biodegradable mounting pad of the present invention, and (l) a biodegradable electrode mounting pad which dissolves and disappears within a patient's body upon contact with human body fluids but only after a post-operative period of time has elapsed which permits the defibrillation function of the pad to have been performed.

BRIEF DESCRIPTION OF THE DRAWINGS

Other objects, advantages and features of the present invention will become apparent from the following specification, drawings and claims in which:

The drawings are not necessarily to scale. Like numbers refer to like parts or steps throughout the drawings.

DETAILED DESCRIPTION OF THE PREFERRED EMBODIMENTS

Figure 1:
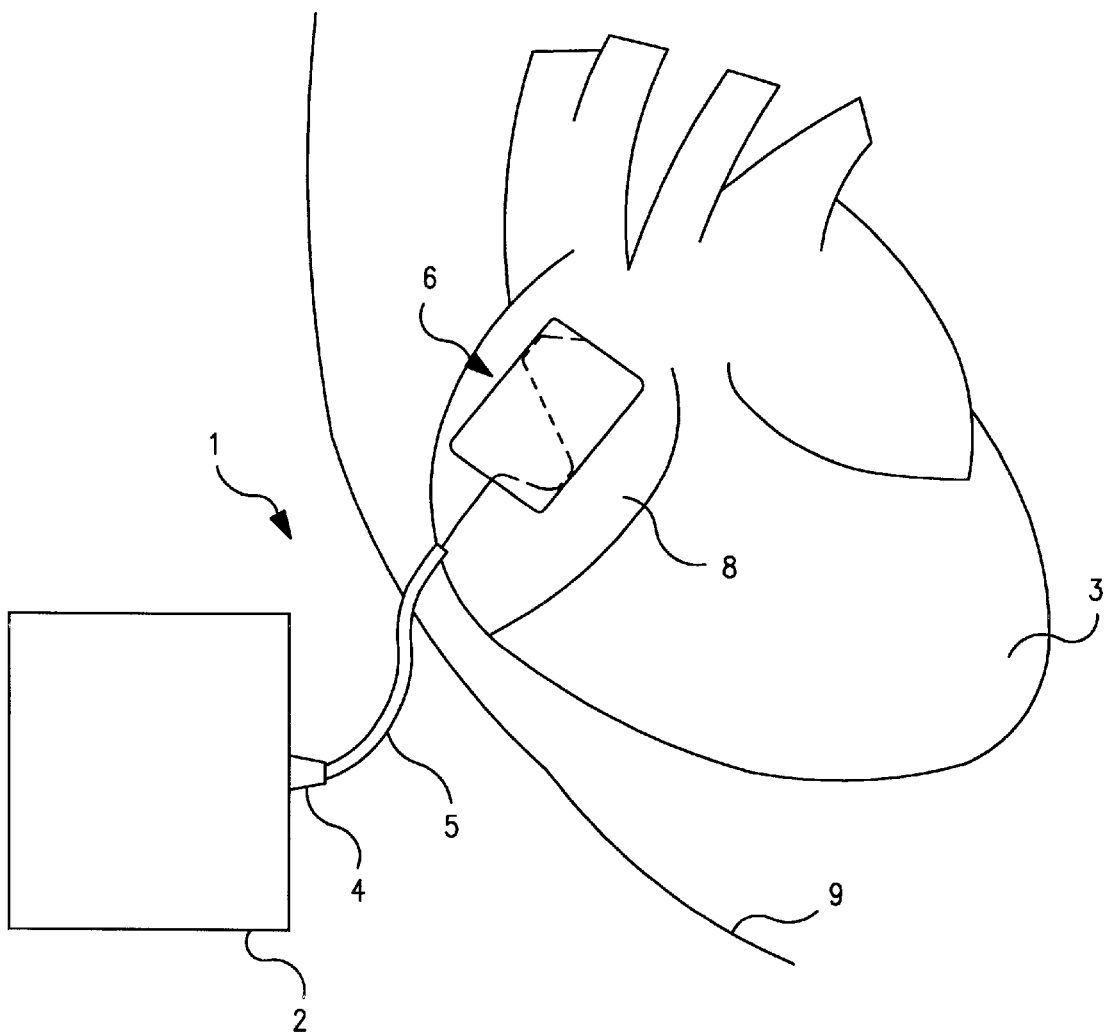
FIG. 1 shows a plan view of one embodiment of a lead of the present invention connected to an external pulse generator and a patient's heart.

FIG. 1 shows a plan view of one embodiment of lead 1 of the present invention. External pulse generator 2 is connected to a patient's heart 3 by lead 1. Lead 1 comprises three sections: connector assembly 4 lead body 5 and electrode assembly 6. Typically two leads are attached to the heart: one to the left atrial wall and another to the right atrial wall. Defibrillation pulses are then delivered across the two electrodes through the left and right atria.

Connector assembly 4 connects lead 1 to external pulse generator 2 which may be, for example, an external pacemaker, external nerve or muscle stimulator, or an external defibrillator. Connector assembly 4 may be similar to any of several well known connector types disclosed in the prior art, such as the break-away needle connectors disclosed in U.S. Patent No. 5,527,358, U.S. Pat. No. 5,871,528 and U.S. Pat. No. 5,792,217, all hereby incorporated by reference herein, each in its respective entirety. Connector assembly 4 may, for example, feature a break-away stainless steel needle having a recess which mates to a finger in a pin assembly. The break-away needle provided on the pin assembly permits the passage of connector assembly 4 from inside the body through the patient's skin to outside of the body. The break-away needle may thereafter be broken off at a breakpoint to permit the pin assembly to be connected to external pulse generator 2.

Alternatively, connector assembly 4 may comprise any of several types well known in the art suitable for electrically connecting the proximal end of lead 1 and the proximal end of electrical conductor 21 to implantable pulse generators such as implantable defibrillators, implantable Pacer-cardio-Defibrillators (PCDs), Implantable Cardio-Defibrillators (ICDs), implantable nerve stimulators, implantable muscle stimulators, implantable gastric system stimulators, and so on. That is, the lead of the present invention is not limited to use with external pulse generators only, but instead also finds application in conjunction with many types of implantable pulse generators.

Figure 2:
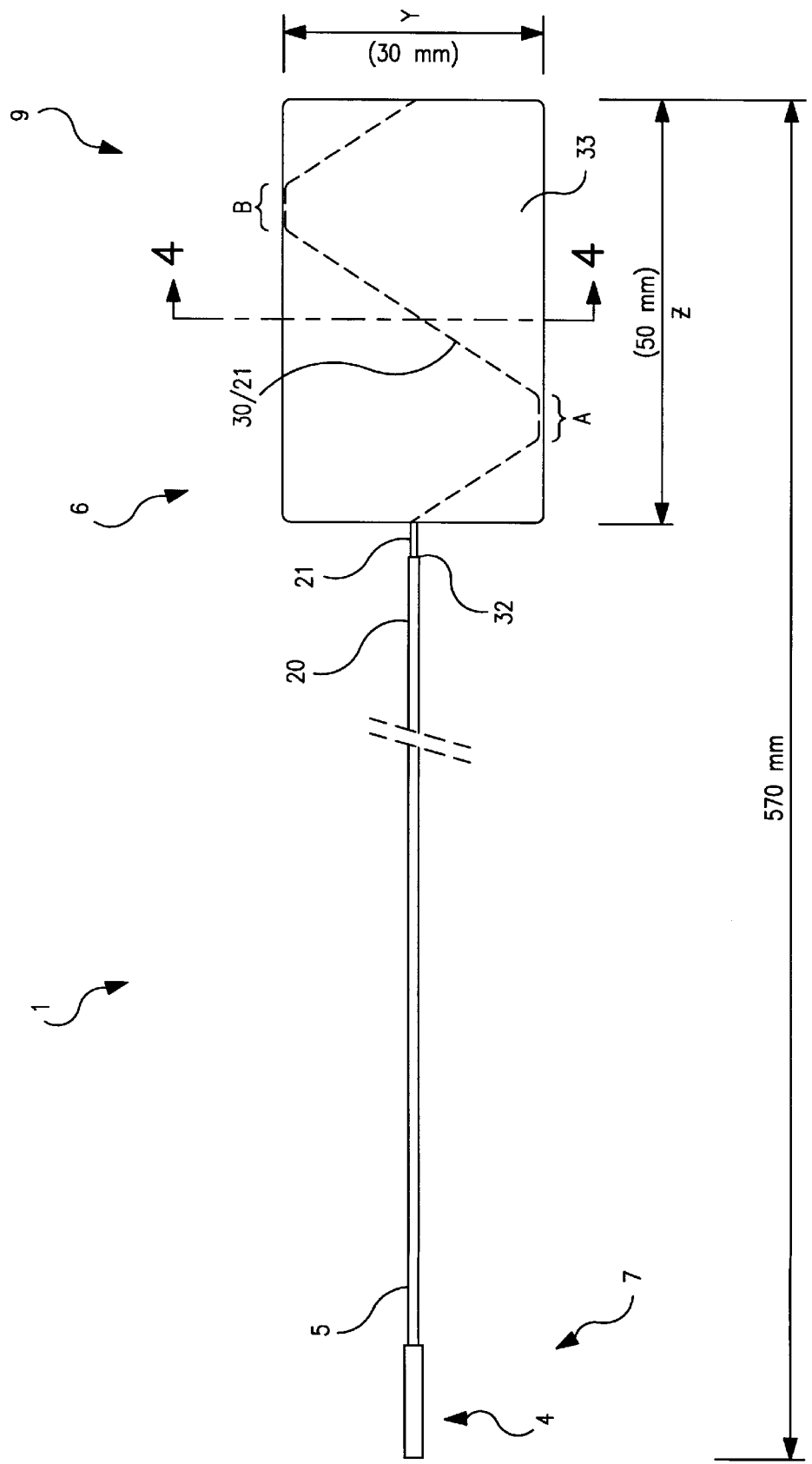
FIG. 2 shows a plan view of one embodiment of a lead of the present invention.

Referring now to FIG. 2, lead body 5 preferably comprises an insulative outer sleeve or sheath 20 having a central lumen, which encases one or more electrical conductors 21. Portions of the lumen forming unfilled gaps, such as gaps between one or more inner conductors 21 may be filled with medical adhesive. Outer sleeve 20 may be constructed from any suitable biocompatible (and preferably biostable) material such as FEP (fluorinated ethylene polymer), PTFE (polytetrafluoroethylene), PEBAX, TEFZEL, polyimide, PVDF (polyvinyldine fluoride), polyurethane, silicone rubber, or any other suitable material.

One or more inner conductors 21 are each constructed in a similar fashion. Thus, the construction of only one such conductor need be described. Inner conductor 21 preferably comprises a plurality of stranded wires, which form electrode wire 30. In a preferred embodiment of the present invention, inner conductor 21 is a multi-filament stainless steel stranded wire. It should be understood, of course, that any suitable material or wire may be employed to form conductor 21 including a coiled wire or any other type of wire made from an acceptable biocompatible material or metal including, but not limited to, such materials as platinum, palladium, titanium, tantalum, rhodium, iridium, carbon, vitreous carbon, and alloys, mixtures, combinations, oxides and/or nitrides of the foregoing. Of course, some materials are incompatible with others and may not be used effectively together. The limitations of specific electrically conductive materials for use with other electrically conductive materials in the context of implantation within the human body are well known in the art.

As best seen in FIG. 2, outer sleeve or insulation 20 terminates at location 32 near the distal end of lead 1. At least one electrical conductor 21 extends between proximal end 7 of lead 1 and distal end 9 of lead 1 and extends distally from the distal end of insulation 20 to terminate near or at distal end 9 of electrode assembly 6. Alternatively, a discrete electrode member may be crimped or otherwise attached to the distal end of at least one electrical conductor 21 and extend distally therefore for attachment to or positioning in or on electrode mounting pad 33. In either embodiment of the present invention, at least one electrical conductor 21 or the discrete electrode member forms an electrode or electrodes for providing electrical stimulation to a patient's heart tissue.

Although FIG. 2 shows only one electrical conductor attached to mounting pad 33, more than one such electrical conductor may be mounted or attached thereto. Note the semi-sinusoidal shape of the distal end of electrical conductor 21 in FIG. 2. Such a shape has been discovered to maximize the surface area of the heart that may be defibrillated by electrode 30 while still maintaining the ability of electrode 30 to be removed from pad 33 through the application of a non-excessive pulling force exerted by a physician upon the proximal end of lead 1 (more about which we say below).

Computer models and animal experiments confirmed the efficacy of the serpentine electrode configuration shown in FIGS. 1 and 2. Two acute animal experiments showed Defibrillation Thresholds (DFTs) obtained with a single wire serpentine electrode of the type shown in FIGS. 1 and 2 were equal to those obtained with a prior art temporary defibrillation lead having three wires or electrodes conforming generally to the lead disclosed in U.S. Pat. No. 5,527, 358 discussed hereinabove. The single wire serpentine electrode of the present invention has the advantages of providing lower material costs, lower manufacturing costs, and being less invasive owing to the smaller diameter of the piercing needle, which it permits.

Figure 3:
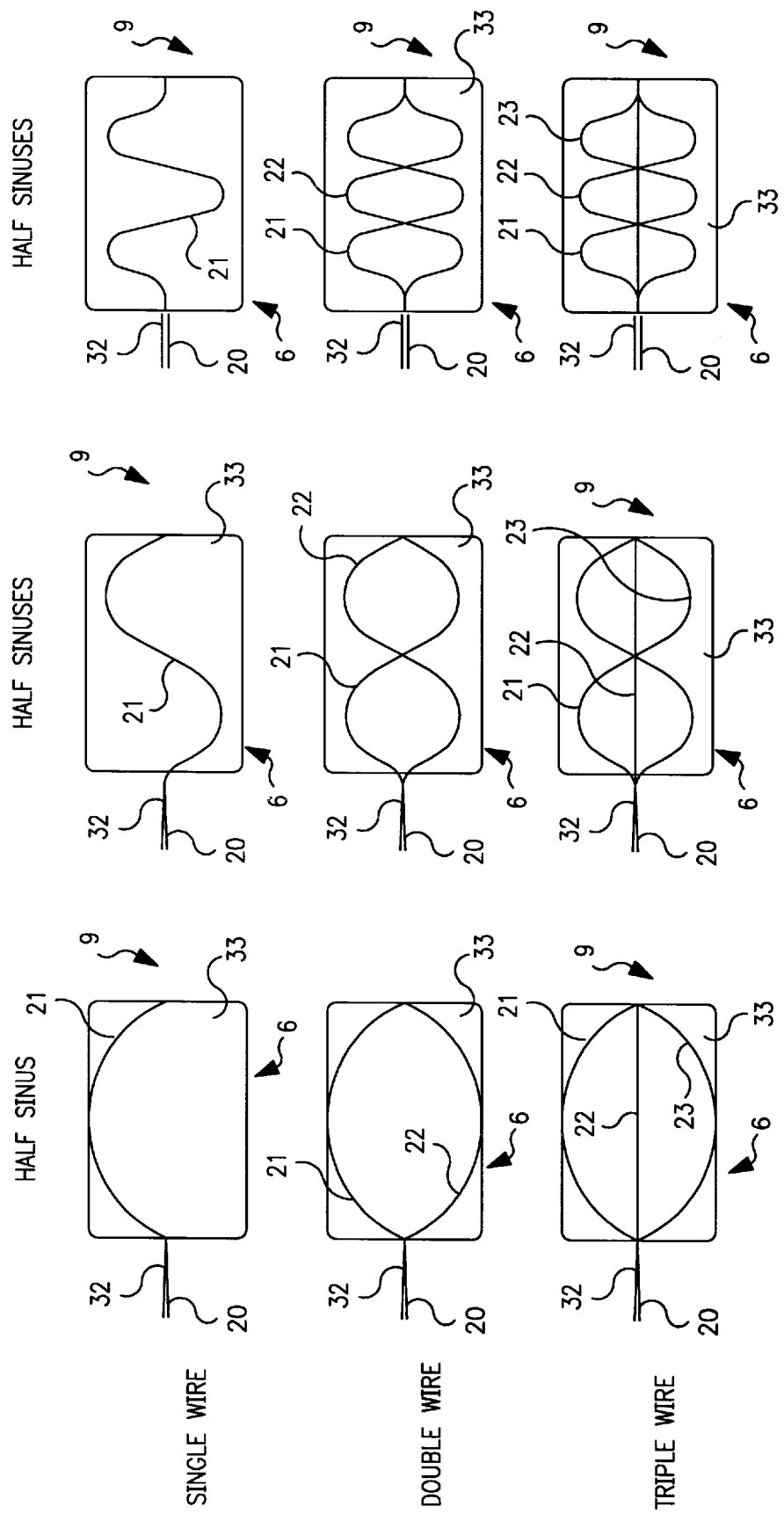
FIG. 3 shows plan views of various embodiments of the distal end of the lead of the present invention.

FIG. 3 shows several different embodiments of electrode assembly 6 of the present invention, including several embodiments where more than one electrical conductor or wire 21 is employed and attached to mounting pad 33. FIG. 3 shows electrical conductors 21, 22 and 23 arranged in various types of sinusoidal, curving or arcing configurations along mounting pad 33.

It is to be noted, however, that the present invention is not limited in scope to embodiments having no more than three electrical conductors disposed on mounting pad 33, and specifically includes within its scope embodiments having more than three such electrical conductors. Additionally, the present invention is not limited in scope to embodiments where the one or more electrical conductors attached to mounting pad 33 assumes a sinusoidally-shaped, arced or curved configuration, but specifically includes within its scope embodiments having straight, triangular, rectangular, linear, non-curved, or non-arcing configurations.

Figure 4:
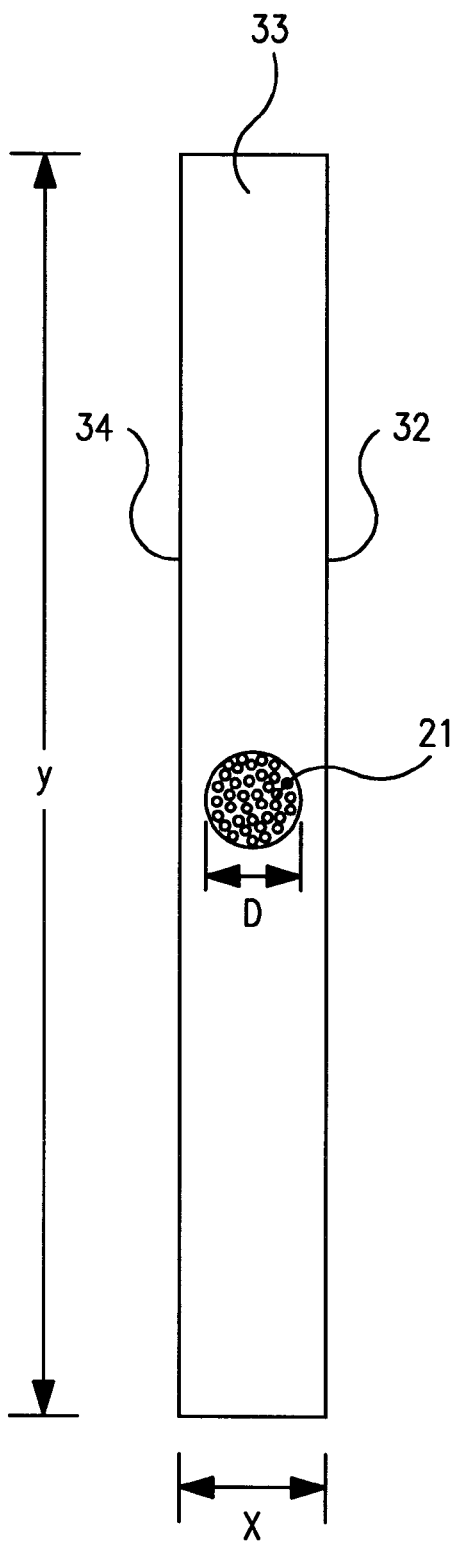
FIG. 4 shows a sectional view of the mounting pad and associated electrode of FIG. 2.

As noted above, electrode assembly 6 most preferably comprises one or more electrical conductors 21 and biocompatible, biostable mounting pad 33. The distal-most portion of each electrical conductor 21, 22 or 23 most preferably has a stranded metallic electrical conductor 30 exposed along the length of mounting pad 33. The distal end of electrical conductor 21 is most preferably disposed between opposing sides 32 and 34 of mounting pad 33, as shown in FIG. 4. In a preferred embodiment of the present invention, electrical conductor 21 is formed of about 49 individual medical grade stainless steel wires which are stranded together to form conductor 21 having a nominal diameter D of about 0.4 mm (see FIG. 4). In less preferred embodiments of the present invention, the wires may be braided or twisted together to form conductor 21.

Continuing to refer to FIGS. 3 and 4, thickness X of mounting pad 33 most preferably ranges between about 2 mm and about 3 mm, but may also range between about 1 mm and about 4 mm, or between about 0.5 mm and about 5 mm. Other thicknesses X and corresponding thickness ranges of mounting pad 33 are also contemplated in the present invention. Mounting pad length Z is most preferably about 50 mm, but may be any other suitable length. Likewise, mounting pad width Y is most preferably about 30 mm, but may be any other suitable width.

In the preferred embodiment of the present invention shown in the drawings hereof, one or more inner conductors 21 are shown mounted within mounting pad 33. It should be understood that such inner conductors may be mounted to mounting pad 33 in any acceptable manner including, without limitation, suturing or gluing all or some of inner conductor 21 to outer surfaces 32 or 34 of mounting pad 33. Holes may further be provided in mounting pad 33, either for the purpose of exposing certain portions of conductor 21 to heart tissue or to reduce the mass of pad 33. Thus, when electrode assembly 6 is attached to cardiac tissue, intermittent sections of the one or more conductors are directly exposed to cardiac tissue through such holes. Mounting pad 33 may further feature suture areas or portions disposed near the corners of pad 33 which permit mounting pad 33 to be sutured directly to heart 3, as best seen in FIG. 1.

In one embodiment of the present invention, mounting pad 33 is constructed and formed from collagen, but may alternatively be fashioned from any suitable biocompatible, biostable, pliant material such as PTFE or PTFE felt. It is a particular advantage of the collagen embodiment of the mounting pad of the present invention that when mounting pad 33 is formed from an appropriate collagenous material, mounting pad 33 dissolves or otherwise dissociates over time following implantation within the human body. Consequently, even after electrode 30/inner conductor 21 is explanted from a patient's body, mounting pad 33 remains implanted within the patient but then disappears over time as it dissolves or otherwise dissociates in the human body fluids with which it comes into contact after being implanted.

Mounting pad 33 is most preferably formed of a collagenous material that maintains its structural integrity long enough to permit the post-operative defibrillation function of lead 1 to be carried out. Once the electrode and lead have been explanted from the patient (typically anywhere between one day to two weeks following the operation in which the lead was initially implanted), mounting pad 33 most preferably begins to dissolve and break down, thereby losing its structural integrity.

Collagen is a natural biopolymer material well suited for use in forming the biodegradable, biocompatible, electrode mounting pad of the present invention. Collagen is the principal structural protein in mammals, constituting approximately one-third of the total body protein. As the chief structural protein of the body, collagen is capable of transmitting tensile and compressive forces of great magnitude. In light of the application of the present invention, such properties are highly desirable. After implantation, a collagen electrode mounting pad of the present invention is enzymatically degraded through the cleavage of peptide bonds by human collagenase. In a preferred embodiment of the present invention, the degradation rate of collagen is controlled by means of crosslinking. Crosslinking may also be employed to enhance the mechanical properties of the electrode mounting pad (more about which we say below), and furthermore beneficially diminishes the antigenicity of the electrode mounting pad.

Other biodegradable, biocompatible materials suitable for use in forming the electrode mounting pad of the present invention include natural materials and their corresponding synthetic equivalents or derivatives, such as albumin, silk, poly(L)lysin, fibrin, elastin, hyaluronic acid preparations, and salts and derivatives thereof such as those described in U.S. Pat. No. 5,128,326, glycos-amino-glycans, polysaccharrides, keratin, chondroitin sulfates, dermatan sulfate, keratan sulfate, heparan, heparan sulfate, heparan substitutes, heparin, heparin substitutes, cellulose and its derivatives, starch, gelatin, dextrans and their derivatives, chitin, chitosan, and combinations or mixtures of, or the products of reactions involving, the foregoing.

Still other natural and synthetic biodegradable, biocompatible materials suitable for use in forming the electrode mounting pad of the present invention include, but are not limited to, aliphatic polyesters, polyamides, polyesteramides, polyorthoesters, polyanhydrides, polyphosphazenes, Poly(glycolic acid), Poly(L-lactic acid), Poly(DL-lactic acid), Poly(p-dioxanone), Poly($_\epsilon$-caprolactone), Poly(3-hydroxypropionic acid), Poly(3-hydroxybutyric acid), Poly($_\alpha$-malic acid), Poly($\beta$-malic acid), Poly(serine ester).

Finally, it is fair to state that yet other natural and synthetic biodegradable, biocompatible materials, whether existing presently or in future, will find application and suitability in forming a biodegradable, biocompatible electrode mounting pad of the present invention.

An electrode mounting pad comprising collagen was constructed using collagen pads obtained from Coletica, a company based in Lyon, France. Those pads were similar to a hemostatic sponge marketed by Coletica in France, Spain and Italy under the mark "HEMOSTAGENE" and distributed in the U.S. by MedChem Products, Inc. under the marks "AVIFOAM" and "ACTIFOAM."

Figure 5:
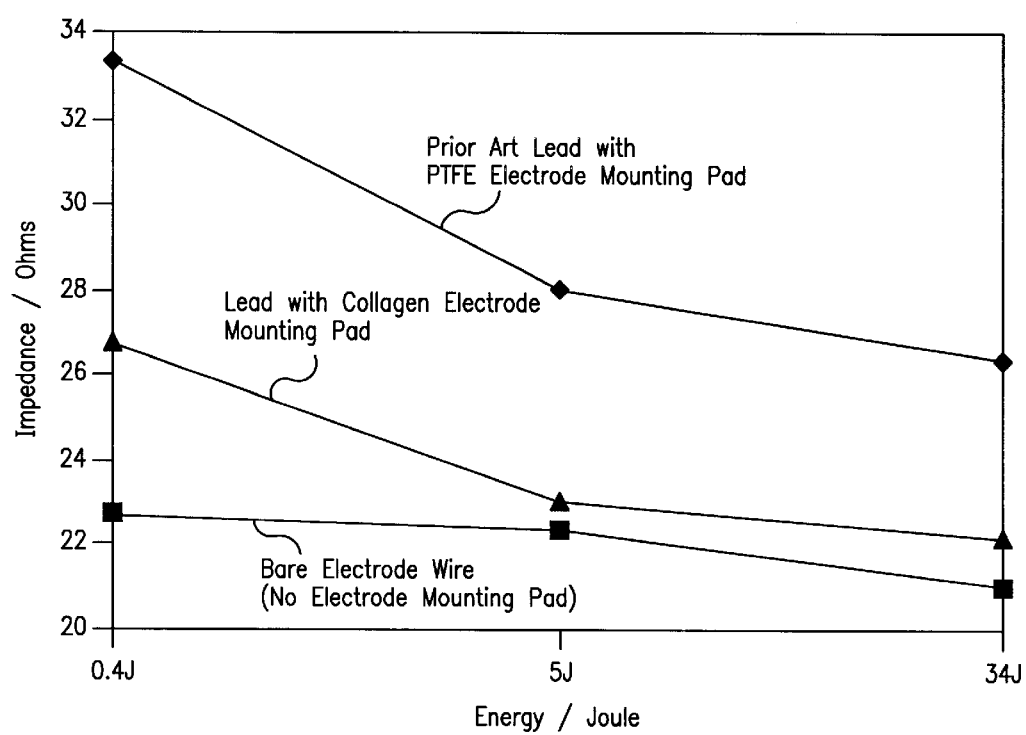
FIG. 5 shows comparative impedance versus energy data for a lead of the present invention and two prior art leads.

In a pre-clinical experiment, impedance measurements were performed to determine the conductivity of the collagen pad. Three different devices were compared: (1) Medtronic Model No. 13004 lead with PTFE electrode mounting pad; (2) Medtronic Model No. 13004 lead with bare wires and no electrode pad, and (3) Medtronic Model 13004 lead with collagen electrode mounting pad. The tested electrodes were positioned in a water bath containing a 0.9% saline solution at room temperature. Electrical shocks were applied between the test electrodes and a Medtronic Model No. 6721M epicardial patch electrode. The distance between the electrodes was set at 49 cm. For the delivery of the electrical shocks a Medtronic DISD Model No. 5358 and a Medtronic Model No. 9790 programmer were employed. Three experimental runs were performed for each tested device. The results of the tests are depicted in FIG. 5. After three hours the tests with the collagen pad were repeated; no significant differences were observed in comparison to the first test results obtained (indicating that the collagen pad was essentially instantaneously hydrated).

FIG. 5 shows that a device having the collagen electrode mounting pad of the present invention has a lower impedance than a device containing a PTFE electrode mounting pad, and further exhibits impedance characteristics comparable to those of a bare electrode wire. In other words, the collagen electrode mounting pad of the present invention provides low lead system impedance, which is a highly desirable feature in a temporary atrial or ventricular defibrillation lead.

After obtaining the foregoing results, several acute implants in sheep were performed to test the feasibility of the new concept in vivo. The study's objective was to determine the DFTs of a lead made according to the present invention, and to determine whether the collagen electrode pad of the present invention was capable of preventing electrical damage to the atrial wall. In a small experiment involving only two implants in sheep, a mean DFT of 120 Volts (i.e., 0.8 Joules) was measured. No acute damage to the atrial walls was observed after shocking 10 times at 288 Volts (i.e., 5 Joules). Fixation of the electrode mounting pad onto the atrial walls was observed to be good. However, immediately after implantation the collagen pads demonstrated major shrinkage with reductions in length and width of about 50%, thereby causing partial exposure of the bare wire electrodes. Such a loss in dimensional integrity was not acceptable, and the underlying cause of the shrinkage was investigated by means of calorimetry to provide detailed information on the heat stability of the collagen material employed to form the electrode mounting pads.

When collagen is heated in a hydrated state it denatures at a specific temperature, resulting in shrinkage of the material. This shrinkage occurs as a result of the macroscopic manifestation of the transformation of collagen's native triple-helix structure to a random coil configuration. Differential scanning calorimetry (DSC) is frequently used to determine the denaturation temperature of collagen materials. DSC determines the difference in energy necessary to keep a sample pan and a reference pan at the same temperature.

The collagen obtained from Coletica to form the electrode mounting pads of the present invention was characterized using a Perkin Elmer DSC. A 5–10 mg collagen sample was placed on a 50 ml aluminum DSC sample pan having a 2 bar maximum internal pressure, after which 5 ml/mg 0.1M phosphate buffer (pH=6.88; 0.05M $Na_2HPO_4$, 0.05M $NaH_2PO_4$) was added to hydrate the collagen. The sample pan was covered with an appropriate cover and the whole was crimp pressed. An empty sample pan was used as the reference. Typically, a run was started at 20° C. (load temperature); after 2 minutes, samples were heated to 80° C., applying a heating rate of 2° C./min. Device software was used to optimize data collection, and to calculate typical properties.

Figure 6:
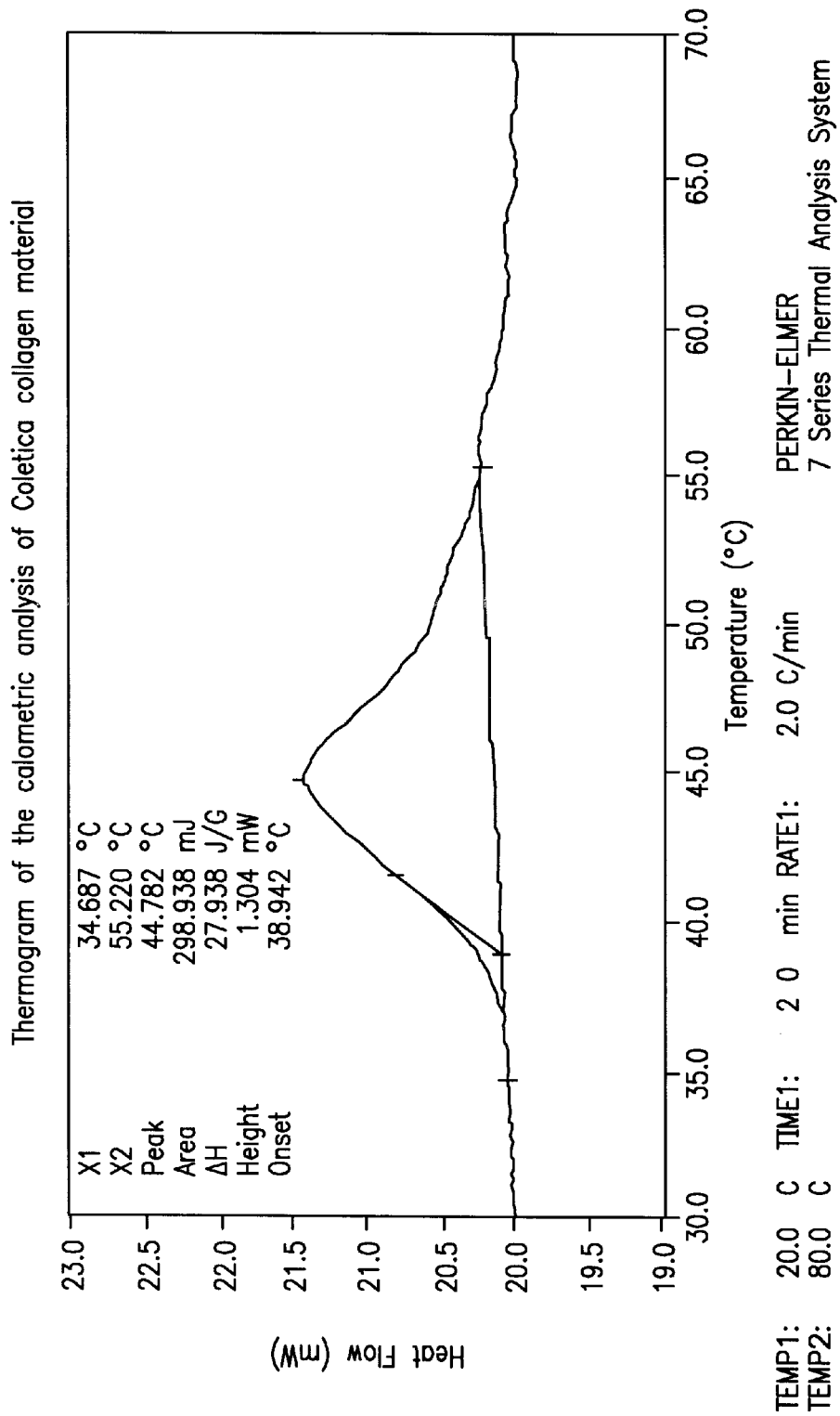
FIG. 6 shows the results of calorimetric analysis of one type of collagen material finding application in the present invention.

The resulting thermogram of FIG. 6 shows a wide peak with significant tailing. Such tailing denotes the heterogeneous character of the tested material, since short triple-helical segments more easily unwrap (or denature) than do long triple-helical segments.

Only a few processes exist that are suitable for sterilizing collagen products. Moist heat (or autoclaving) cannot be used to sterilize collagen because the hydrated protein is susceptible to thermal denaturation. Gaseous ethylene oxide (ETO) sterilization may be employed to sterilize collagen under moistened conditions, elevated temperatures and pressures. If the temperatures employed in ETO sterilization are not excessive, little helical denaturation occurs. Ethylene oxide reacts with the collagen. Losses of the amino acids lysine and hydroxylysine, in particular, suggest that free amino groups participate in the reaction with ethylene oxide. There is little doubt that such reactions may affect the physical and biological properties of the collagen. Consistency in the treatment and sterilization of collagen materials is therefore important.

E-beam or alpha-irradiation may also be employed to sterilize collagen products. It has, however, been shown conclusively that such methods of sterilizing collagen have a significant impact on the stability of collagen. Depending on the particular product application, therefore, irradiation/sterilization of collagen may not be appropriate.

DSC techniques were next employed to determine the relative efficacies of the three foregoing sterilization methods (i.e., ETO, E-beam and alpha-irradiation sterilization). The results obtained are shown in Table 1 below, where it becomes obvious that sterilization per se lowers the denaturation temperature of collagen material. All temperatures shown in Table 1 are in Degrees Celsius.

U.S. patent application for "Temporary Medical Electical Lead Having Biodegradable Electrode Mounting Pad" to Van Wijk et al.

TABLE 1

Effect Of Sterilization on Heat Stability of Collagen

| Type of Material | Peak Start Temp. | Peak End Temp. | Peak Temp. | Onset Temp.* |
|---|---|---|---|---|
| Control (non sterilized) | 36.4 | 59.9 | 44.2 | 39.6 |
| Gamma sterilized | 28.3 | 52.1 | 38.7 | 33.0 |
| E-beam sterilized | 31.3 | 50.0 | 39.4 | 35.4 |
| ETO sterilized | 35.0 | 57.1 | 40.9 | 37.2 |

*Onset temperature is the temperature at which the tangent in the inflection point crosses the baseline.

As Table 1 shows, and in comparison to the control material, ETO sterilization was observed not to change the heterogeneity of the collagen material, whereas both E-beam and ã-irradiation seem to decrease the heterogeneous character of collagen material (by exhibiting less DSC tailing). The foregoing observations in combination with the lowering of the peak start temperatures confirm that chain-scission occurs in collagen molecules, whereby shorter triple helix segments are introduced into the collagen fibers. Those shorter segments unwrap more easily during heating.

As discussed above, ETO sterilization chemically modifies collagen. The chemical modification resulting from ETO sterilization may reduce the stability of triple helix segments such that collagen denaturation is facilitated. The thermogram of FIG. 6 shows that denaturation of ETO sterilized collagen begins at a temperature, which is below the normal body temperature of a human subject. Our calorimetric data help explain the findings of the first acute implant study, in which the collagen pad demonstrated major shrinkage upon contact with the atrial wall. Thus, ETO sterilization of collagen is the most preferred of the three investigated sterilization methods.

Table 2 below shows results obtained using a crosslinked collagen material, where all temperatures are in Degrees Celsius. As Table 3 shows, crosslinking of collagen increases its denaturation temperature. Collagen's triple helix structure is stabilized by hydrogen bonds, which are heat unstable. Introduction of covalent crosslinks increases the stability of the triple helix, and thus increases the denaturation temperature. In the present invention, physical or chemical crosslinking methods may be employed to crosslink collagen-based materials. In addition to the increase in denaturation temperature, crosslinking also enhances the resistance to biodegradation of the material, suppresses its antigenicity and improves its mechanical properties.

As discussed above, major shrinkage of non-crosslinked collagen electrode mounting pads was observed to occur after the pads were positioned in vivo on the atrial wall. Such losses in dimensional integrity were deemed unacceptable. Crosslinking with a water-soluble carbodiimide was thus performed as a means to increase the denaturation temperature and enhance the in vivo stability of the collagen electrode mounting pad. The method of carbodiimide crosslinking was selected for its ease of operation and because carbodiimide crosslinked collagen materials generally demonstrate suitable biocompatibility properties. Our objective was to achieve an onset of the denaturation temperature slightly above body temperature between about 40° C. and about 45° C. Crosslinking specifications were set to limit the impact crosslinking would have on the biodegradation characteristics of the collagen material.

Next, calorimetry techniques were employed to permit optimization of the crosslink process. After the collagen material was exposed to various concentrations of selected crosslinking reagents, the consequent change in denaturation temperature was determined (see Table 2 below). Crosslinked materials were also ETO sterilized to determine and take into account the decrease in denaturation temperature ETO sterilization causes.

In the crosslinking process employed to acquire the data shown in Table 2 below, a collagen pad measuring about 50×30 mm and having a mass of about 0.5 grams was first hydrated in a PP beaker holding 50 ml of a 0.25M MES buffer solution (adjusted to pH=5.0 by dropwise addition of 1 N NaOH). After 30 minutes the collagen pad was withdrawn from the solution and carefully positioned on lint-free towels to permit excess buffer solution to drain away. Next, 50 ml of a 0.25M MES buffered solution (pH=5.0) containing crosslinking reagents EDC (3-ethyl-1-(diaminopropyl) carbodiimide HCl) and NHS (N-hydroxy succinimide) prepared, and within 5 minutes after adding EDC and NHS to the buffered solution the collagen pad was immersed therein. Crosslinking was permitted to proceed for 2 hours while gently shaking the buffered solution. Following crosslinking, the electrode mounting pad was first washed in distilled water three times for 15 minutes, then rinsed washed in a solution containing 0.1M $NaH_2PO_4$ for 2 hours, and then rinsed three times in distilled water for 15 minutes. Finally, the crosslinked collagen electrode mounting pad had excess water drained therefrom and was placed in a freezer at a temperature below −70° C. Once completely frozen, the collagen pad was freeze dried overnight.

U.S. patent application for "Temporary Medical Electical Lead Having Biodegradable Electrode Mounting Pad" to Van Wijk et al.

TABLE 2

Effect of Crosslinking on the Heat Stability of Collagen

| Sample | Crosslinking Level | | Peak Start Temp. | Peak End Temp. | Peak Temp. | Onset Temp. |
| --- | --- | --- | --- | --- | --- | --- |
| | EDC [µM] | NHS [µM] | | | | |
| A | 60000 | 24000 | 66.2 | 82.2 | 77.7 | 68.4 |
| B | 12000 | 12000 | 53.8 | 74.2 | 65.8 | 60.5 |
| C | 6000 | 6000 | 57.4 | 67.9 | 64.0 | 60.6 |
| D | 3000 | 3000 | 56.6 | 65.4 | 61.4 | 58.7 |
| E | 1000 | 1000 | 49.2 | 65.2 | 54.7 | 50.3 |
| F | 100 | 100 | 39.9 | 65.9 | 49.9 | 44.3 |
| G | 10 | 10 | 38.6 | 65.2 | 47.6 | 42.8 |
| Control | 0 | 0 | 36.4 | 59.9 | 44.2 | 39.6 |

Figure 7:
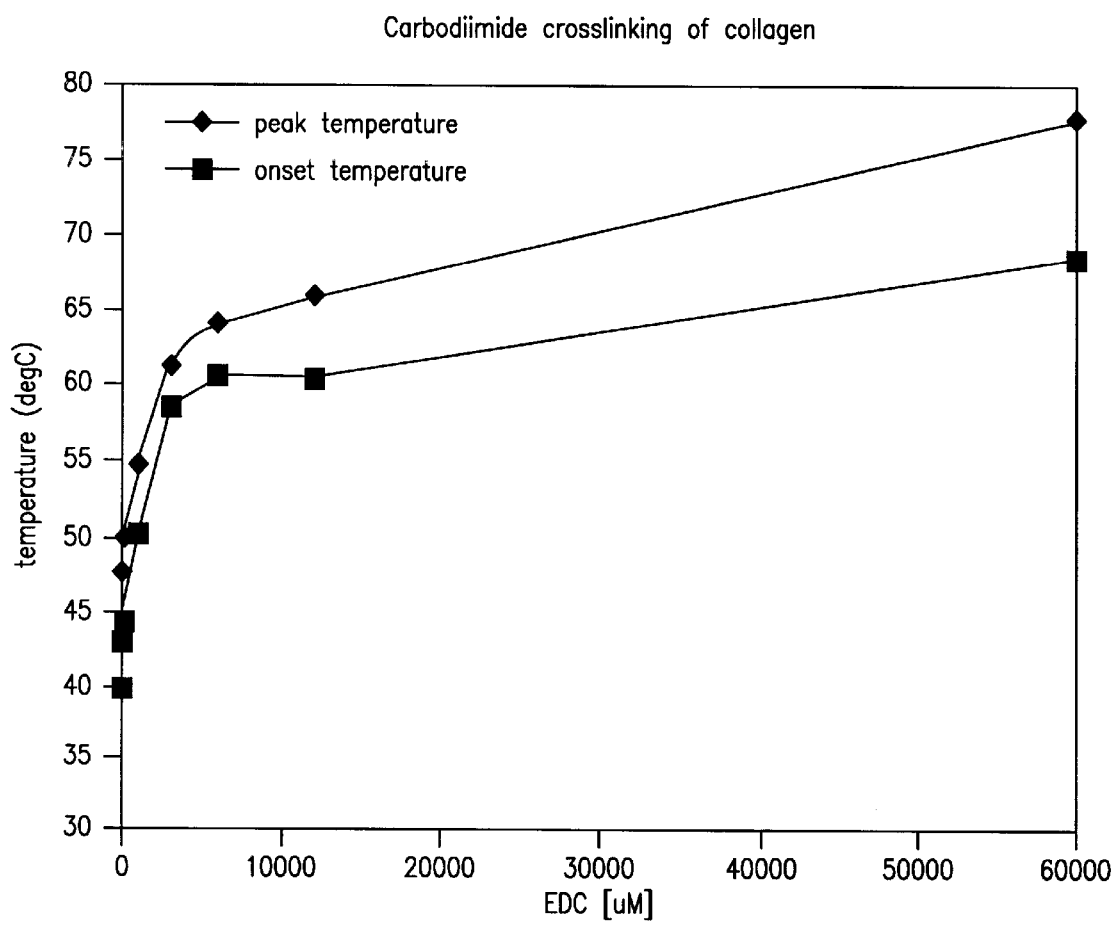
FIG. 7 shows the increase in the onset of the denaturation temperature, which occurs in a crosslinked collagen material of the present invention.

Data corresponding to Table 2 above are shown in FIG. 7, where it is shown that an immediate increase in the onset of the denaturation temperature occurs in crosslinked collagen materials of the present invention, even at low reagent concentrations. As discussed above, an increase in denaturation temperature is directly related to enhanced resistance of biodegradation. Thus, an initial temperature ranging between about 43° C. and about 45° C. at which denaturation begins to occur was determined to provide satisfactory results in at least some embodiments of the present invention. In the light of such considerations, further experiments were conducted using collagen materials made according to the conditions and specifications corresponding to Sample F in Table 2. Materials conforming to the conditions and specifications of Sample F were chosen over those corresponding to Sample G because ETO sterilization lowers the temperature at which the onset of denaturation occurs.

Next, the effects of ETO sterilization on crosslinked collagen electrode mounting pads was determined by calorimetric means. Table 3 below shows the results obtained, where all temperatures are in Degrees Celsius.

U.S. patent application for "Temporary Medical Electical Lead Having Biodegradable Electrode Mounting Pad" to Van Wijk et al.

TABLE 3

Effect of Sterilization on Heat Stability of Collagen

| Type of Material | Peak Start Temp. | Peak End Temp. | Peak Temp. | Onset Temp. |
| --- | --- | --- | --- | --- |
| Crosslinked F (non sterilized) | 39.4 | 61.7 | 49.2 | 43.7 |
| Crosslinked F (ETO sterilized) | 38.6 | 61.7 | 48.3 | 41.6 |

In combination with the results shown in Table 2 above, Table 3 shows that crosslinking collagen electrode mounting pads using the conditions and specifications corresponding to sample F results in collagen denaturation temperatures which prevent or at the very least substantially impede in vivo shrinkage of the electrode mounting pad of the present invention.

Next we determined by in vitro collagen digestion means whether the crosslinked collagen material of the present invention made according to the optimum crosslinking techniques and parameters described above affected enzyme degradation profiles significantly in respect of non-crosslinked control collagen materials. To that end we obtained enzyme degradation profiles for non-crosslinked control collagen materials as well as for collagen materials made according to the specifications and processes corresponding to crosslinked collagen Sample F described above.

Our experimental procedures for in vitro collagen digestion were as follows. First, the weight of individual collagen strips was recorded. A collagenase stock solution was prepared, after which 5 ml aliquots were immediately frozen at a temperature less than–18° C. The collagenase stock solution was a 0.1 M Tris-HCl (Sigma Chemie, Bornem, Belgium) buffered solution having a pH of 7.4, containing 5 mM $CaCl_2$ (Acros Chimica, Geel, Belgium), 0.05 mg/ml $NaN_3$ (Merck-Schuchardt, Darmstadt, Germany), and 10 U/ml collagenase (EC 3.4.24.3; from Clostridium histolyticum; type IA, 550 units/mg solid; Sigma Chemie, Bornem, Belgium). Prior to use the aliquots were thawed. Collagen strips (n=3; approx. 0.05 g) were subjected to collagenase digestion by immersion of the individual strips in 5 ml of collagenase solution at 37° C. (collagenase: collagen=1 U/mg). After 1 hour, collagenase digestion was terminated by adding 0.5 ml of 0.25 M EDTA (99%; Acros Chimica, Geel, Belgium). Thereafter, the strips were rinsed three times for 5 minutes in 0.1 M Tris-HCl having a pH of 7.4, after which the strips were rinsed a further three times for 5 minutes in distilled water. Finally, the strips were frozen for 2 hours at about–80° C. and freeze-dried overnight. Thereafter, the weight of each strip was determined and the weight loss of each recorded. Digestion was continued as above until complete dissolution of the collagen strips occurred.

Figure 8:
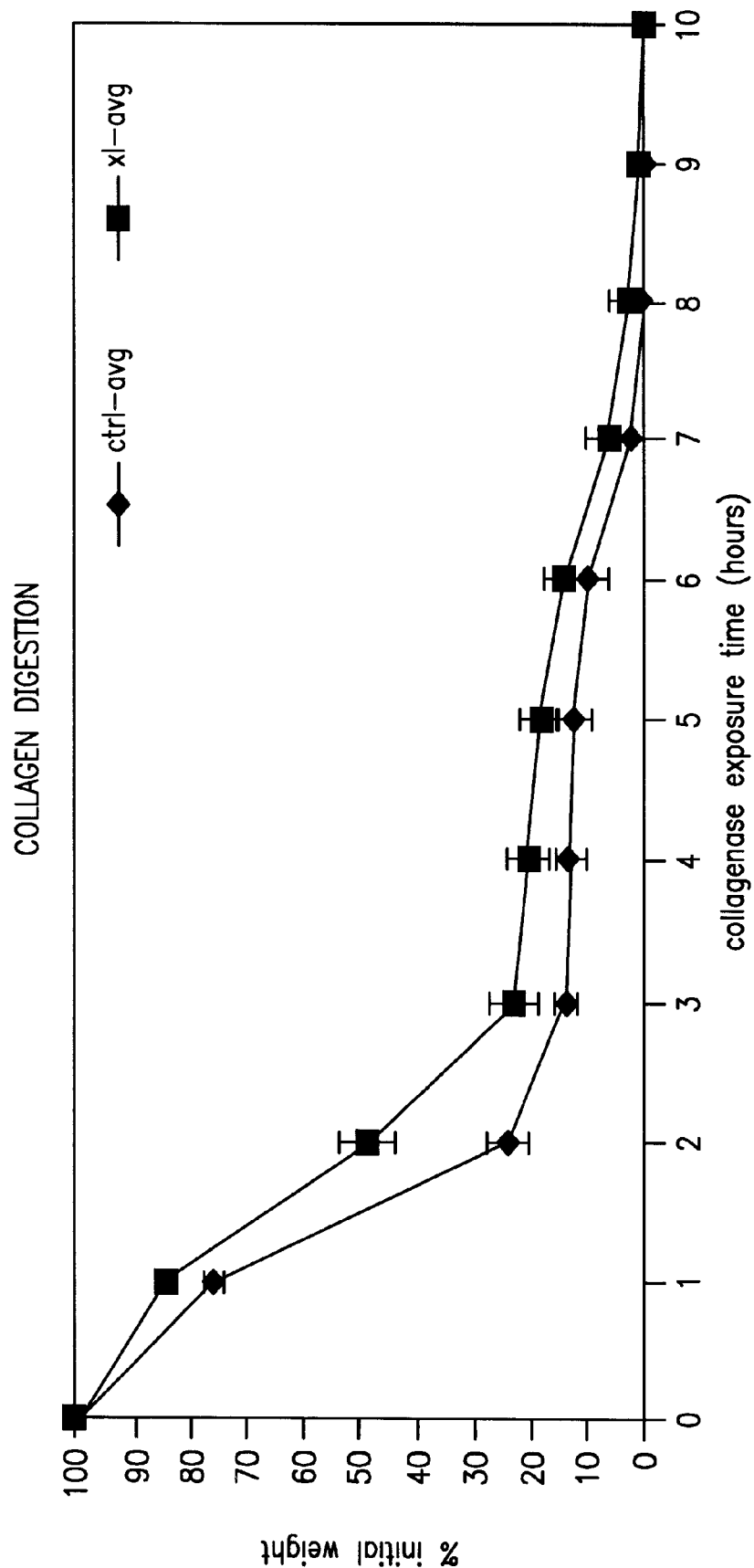
FIG. 8 shows comparative digestion profiles for crosslinked and non-crosslinked collagen materials.

FIG. 8 shows the degradation profiles obtained for the control (i.e., non-crosslinked) collagen samples and the crosslinked collagen samples made according to the conditions and specifications of Sample F. FIG. 8 shows that crosslinked collagen samples of the present invention take slightly longer to degrade than do non-crosslinked collagen samples. The increase in the amount of degradation time is very slight, however. Such a slight increase in degradation time is consistent with our initial objective of introducing a level of crosslinking in collagen, which did not appreciably affect the biodegradation characteristics of the collagen.

Another observed feature of crosslinked collagen samples in comparison to non-crosslinked samples was that degradation seemed to be changed into a surface erosion process in the crosslinked samples (as opposed to the bulk erosion processes noted in non-crosslinked samples). Unlike the early fragmentation observed in the non-crosslinked control samples, the crosslinked samples maintained their original shapes almost until the end of each experiment. Such degradation characteristics of crosslinked collagen materials may be highly advantageous in respect of maintaining the dimensional integrity of a collagen pad during the functional lifetime of an implanted temporary defibrillation lead.

In accordance with the foregoing observations and teachings, collagen electrode mounting pads appear to be much more suitable for use in temporary implantable defibrillation leads than do prior art PTFE felt electrode mounting pads. One chief advantage of the collagen electrode mounting pad of the present invention is the fact that a collagen pad is resorbed into the body over time so that eventually no foreign material remains in the body. Moreover, varying the degree or amount of crosslinking, which is permitted to occur in the collagen, may control the rate at which degradation of the electrode mounting pad of the present invention proceeds when implanted within the human body.

Yet another advantage of the collagen electrode mounting pad of the present invention is the demonstrated improvement in increased conductivity (or lowered impedance) obtained with a collagen electrode mounting pad in respect of a PTFE felt electrode mounting pad. Moreover, although the conductivity of the collagen electrode mounting pad is similar to that of a bare wire, one preferred embodiment of the collagen electrode pad of the present invention helps to minimize tissue damage since the atrial wall is not permitted to directly come into contact with the defibrillation electrode (which is disposed within a matrix of surrounding collagen—see FIG. 4).

Figure 9:
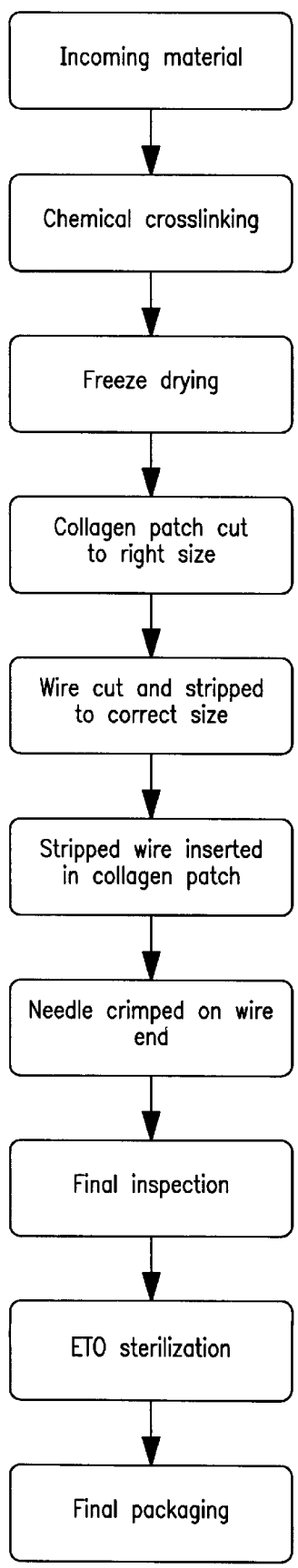
FIG. 9 illustrates one method of making a lead of the present invention.

FIG. 9 shows one method of the present invention for making a temporary defibrillation lead. After the collagen electrode mounting pad has been crosslinked, freeze dried, and cut to the proper dimensions, electrode wire/conductor 30/21 is most preferably woven through the collagen matrix using a needle. After electrode wire 30/conductor 21 has been appropriately placed in electrode mounting pad 33, break-away connector assembly 4 and its corresponding piercing needle are crimped to proximal end 4 of the lead body.

Referring now to FIG. 2, when electrode wire 30/at least one electrical conductor 21 is threaded by needle means through the collagen matrix of electrode mounting pad 33, collagen/electrode mounting pad 33 is sliced in regions A and B to permit electrode wire/conductor 21 to be re-inserted by hand into the collagen matrix in a different direction or orientation.

In another embodiment and method of the present invention, electrode wire 30/at least one electrical conductor 21 is appropriately placed and oriented in an electrode mounting cast, and a collagen-containing solution is poured therein which at least partially, if not entirely, surrounds or encases electrode wire 30/at least one electrical conductor 21. After being subjected to suitable crosslinking, dehydration and/or freeze drying processes, the collagen electrode mounting pad containing electrode 30/conductor 21 is removed from the cast and the lead is subjected to any further processing which may be required.

Figure 10:
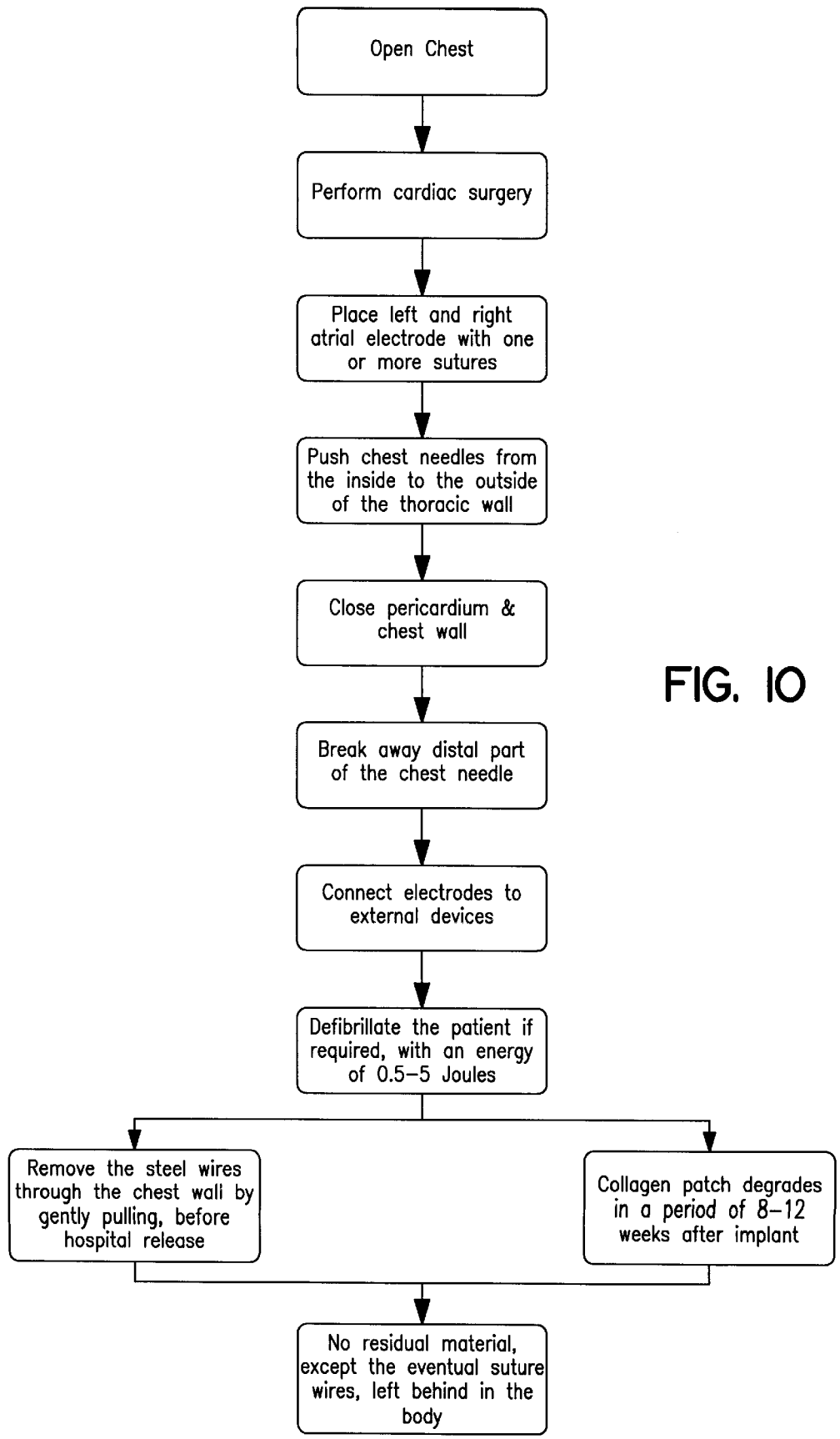
FIG. 10 illustrates one method of implanting and removing a lead of the present invention.

Referring now to FIGS. 1 and 10, in one method of the present invention implantation of lead 1 proceeds as follows. Electrode mounting pad 33 is sutured to atrium 8 using suture areas 35. Next, connector assembly 4 is exteriorized at a point away from the incision through the use of a break-away needle and pin assembly known in the art (see, for example, U.S. Pat. No. 5,527,358 entitled "Temporary Medical Electrical Lead" to Mehmanesh et al.). The needle is used to pierce the skin from the interior to the exterior so as to the pin assembly. Once lead 1 is satisfactorily sutured to the atrium, the pin assembly is exposed and the lead is connected to external pulse generator 2. The incision in the patient may then be closed. At this point lead 1 can deliver therapeutic electrical pulses, including defibrillating, cardioverting or pacing pulses, to atrium 8. Note that in the present invention an implantable pulse generator may be substituted for external pulse generator 2.

One important aspect of the lead of the present invention is the ease with which it may be removed from a patient within which it has been implanted. Conductor 21/electrode 30 is mounted within mounting pad 33 so that it may be removed, even once implanted, through the application of tractional or gentle pulling forces. That is, the distal end of conductor 21 affixed to mounting pad 33 may be gently removed therefrom through the application of a tractional force upon proximal end 5 of lead 1. Alternatively, and depending upon various factors such as the amount of time mounting pad 33 has been implanted within the patient and the degree of crosslinking which has been permitted to occur in mounting 33 during the manufacturing process, explantation of conductor 21 from the patient may require the application of almost no tractional force owing to electrode pad 33 having been resorbed or dissolved in the patient's body by the time conductor 21 is explanted.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to the use of any particular specific configuration of temporary defibrillation or pacing lead or electrode shown explicitly in the drawings hereof. The electrode mounting pad of the present invention need not be made of collagen, but may be formed from any other suitable biodegradable, biocompatible material which provides substantially the same function as the collagen electrode mounting pads disclosed explicitly herein. Although crosslinked collagens are preferred for the electrode mounting pad of the present invention, non-crosslinked collagen materials may also be used. Additionally, the stimulating electrode employed in conjunction with the present invention need not be a single wire or a single electrode attached to a single electrical conductor. Those skilled in the art will understand immediately that many variations and permutations of known electrical conductor/stimulating electrode configurations may be employed successfully in the present invention.

The present invention is also not limited to use in conjunction with temporary defibrillation or cardioversion leads, but may also be employed as a temporary pacing lead in bradycardia applications, as a cardiac sensing lead only, as a fetal monitoring and/or sensing lead, a fluoroless lead, a balloon lead, or a lead for use in stent implantation or other surgical procedure where cardiac backup, pacing support or defibrillation is required.

In the claims, means plus function clauses are intended to cover the structures described herein as performing the recited function and their equivalents. Means plus function clauses in the claims are not intended to be limited to structural equivalents only, but are also intended to include structures which function equivalently in the environment of the claimed combination.

All printed publications and patents referenced hereinabove are hereby incorporated by referenced herein, each in its respective entirety.

We claim:

1. A temporary medical electrical lead for pacing or defibrillating a heart of a patient, the lead having distal and proximal ends, comprising:
   (a) a lead body having proximal and distal ends, comprising:
      (i) a single electrical conductor having proximal and distal ends;
      (ii) an insulative sheath formed of biocompatible and electrically insulative material, the sheath extending over and covering at least portions of the electrical conductor, the sheath not being disposed over at least a distal-most end of the single electrical conductor;
   (b) an electrical connector assembly attached to the proximal end of the single electrical conductor for attachment to a device capable of providing pacing or defibrillation pulses therethrough, and
   (c) an electrode mounting pad comprising lower and upper surfaces separated by a pad thickness, the pad having outer edges disposed between the lower and upper surfaces, the lower surface being configured for engagement with an outer surface of a human heart, the electrode mounting pad being disposed near the distal end of the lead body, the distal end of the single electrical conductor being attached to or integrated into the electrode mounting pad such that all portions of the distal end of the conductor are disposed at locations disposed upwardly from the lower surface such that no such portions of the conductor distal end penetrate the lower surface of the electrode mounting pad, the distal end of the single electrical conductor forming a sinusoidally-shaped or semi-sinusoidally shaped electrode disposed on or in the electrode mounting pad such that at least portions of the sinusoidally-shaped or semi-sinusoidally shaped electrode are disposed along the outer edges of the electrode mounting pad and such that the electrode may be removed from a patient's body after implantation therein through the application of a pulling force exerted by a physician, the electrode mounting pad comprising a biodegradable, biocompatible material soluble in human body fluids.

2. The temporary medical electrical lead of claim 1, wherein the single electrical conductor comprises a plurality of stranded or braided stainless steel wires.

3. The temporary medical electrical lead of claim 1, wherein the insulative sheath is formed from one of FEP, PTFE, urethane, polyurethane, silicone rubber, PEBAX, PVDF, TEFZEL, polyimide, and combinations or mixtures thereof.

4. The temporary medical electrical lead of claim 1, wherein the electrode mounting pad has one or more holes disposed therethrough.

5. The temporary medical electrical lead of claim 1, wherein the electrode mounting pad has a thickness ranging between one of about 2 mm and about 3 mm, about 1 mm and about 4 mm, and about 0.5 mm and about 5 mm.

6. The temporary medical electrical lead of claim 1, wherein the electrical connector assembly comprises a break-away piercing needle.

7. The system of claim 1, wherein the biodegradable, biocompatible material comprises collagen.

8. The system of claim 7, wherein the biodegradable, biocompatible material comprises crosslinked collagen.

* * * * *